(12) United States Patent
Shener

(10) Patent No.: US 9,179,821 B2
(45) Date of Patent: *Nov. 10, 2015

(54) SYSTEM FOR USE IN SURGICAL PROCEDURES

(71) Applicant: Smith & Nephew, Inc., Memphis, TN (US)

(72) Inventor: Cemal Shener, Woburn, MA (US)

(73) Assignee: Smith & Nephew, Inc., Memphis, TN (US)

(*) Notice: Subject to any disclaimer, the term of this patent is extended or adjusted under 35 U.S.C. 154(b) by 77 days.

This patent is subject to a terminal disclaimer.

(21) Appl. No.: 13/759,217

(22) Filed: Feb. 5, 2013

(65) Prior Publication Data

US 2013/0155213 A1      Jun. 20, 2013

Related U.S. Application Data

(63) Continuation of application No. 12/710,431, filed on Feb. 23, 2010, now Pat. No. 8,388,515.

(60) Provisional application No. 61/157,391, filed on Mar. 4, 2009.

(51) Int. Cl.
```
A61B 1/04      (2006.01)
A61B 1/12      (2006.01)
A61B 1/00      (2006.01)
A61B 1/015     (2006.01)
A61B 1/313     (2006.01)
```
(52) U.S. Cl.
CPC .............. *A61B 1/00002* (2013.01); *A61B 1/015* (2013.01); *A61B 1/12* (2013.01); *A61B 1/313* (2013.01)

USPC ........... 600/109; 600/118; 600/157; 600/158; 348/65

(58) Field of Classification Search
USPC ............. 600/109, 118, 117, 157, 158; 348/65
See application file for complete search history.

(56) References Cited

U.S. PATENT DOCUMENTS

| | | | |
|---|---|---|---|
| 4,622,584 A | 11/1986 | Nagasaki et al. | |
| 5,368,015 A | 11/1994 | Wilk | |
| 5,868,666 A | 2/1999 | Okada et al. | |
| 5,931,808 A | 8/1999 | Pike | |

(Continued)

FOREIGN PATENT DOCUMENTS

| | | |
|---|---|---|
| EP | 0340145 A1 | 11/1989 |
| EP | 1911474 A1 | 2/2013 |
| WO | 2008028149 A2 | 3/2008 |

OTHER PUBLICATIONS

International Search Report and Written Opinion for PCT/US2010/024978 dated May 7, 2010.

(Continued)

*Primary Examiner* — Rochelle-Ann J Blackman
(74) *Attorney, Agent, or Firm* — Chapin IP Law, LLC

(57) ABSTRACT

The present disclosure relates to a system for use in surgical procedures. The system includes an endoscope; an imaging device coupled to the endoscope; an imaging processor coupled to the imaging device; and at least one management system coupled to the imaging processor, wherein a function of the management system is automatically adjusted upon receipt of a communication from the imaging processor. A method of adjusting an image of a surgical site during a surgical procedure is also disclosed.

14 Claims, 1 Drawing Sheet

(56) References Cited

U.S. PATENT DOCUMENTS

| | | |
|---|---|---|
| 6,881,188 B2 | 4/2005 | Furuya et al. |
| 8,388,515 B2 * | 3/2013 | Shener .......................... 600/109 |
| 2005/0119527 A1 | 6/2005 | Banik et al. |
| 2006/0047184 A1 | 3/2006 | Banik et al. |
| 2006/0069306 A1 | 3/2006 | Banik et al. |
| 2007/0249993 A1 | 10/2007 | Mollstam et al. |
| 2008/0183080 A1 | 7/2008 | Abraham |

OTHER PUBLICATIONS

Australian Government, Patent Examination Report No. 1 for Patent Application 2010221656, Nov. 28, 2014, pp. 3.

* cited by examiner

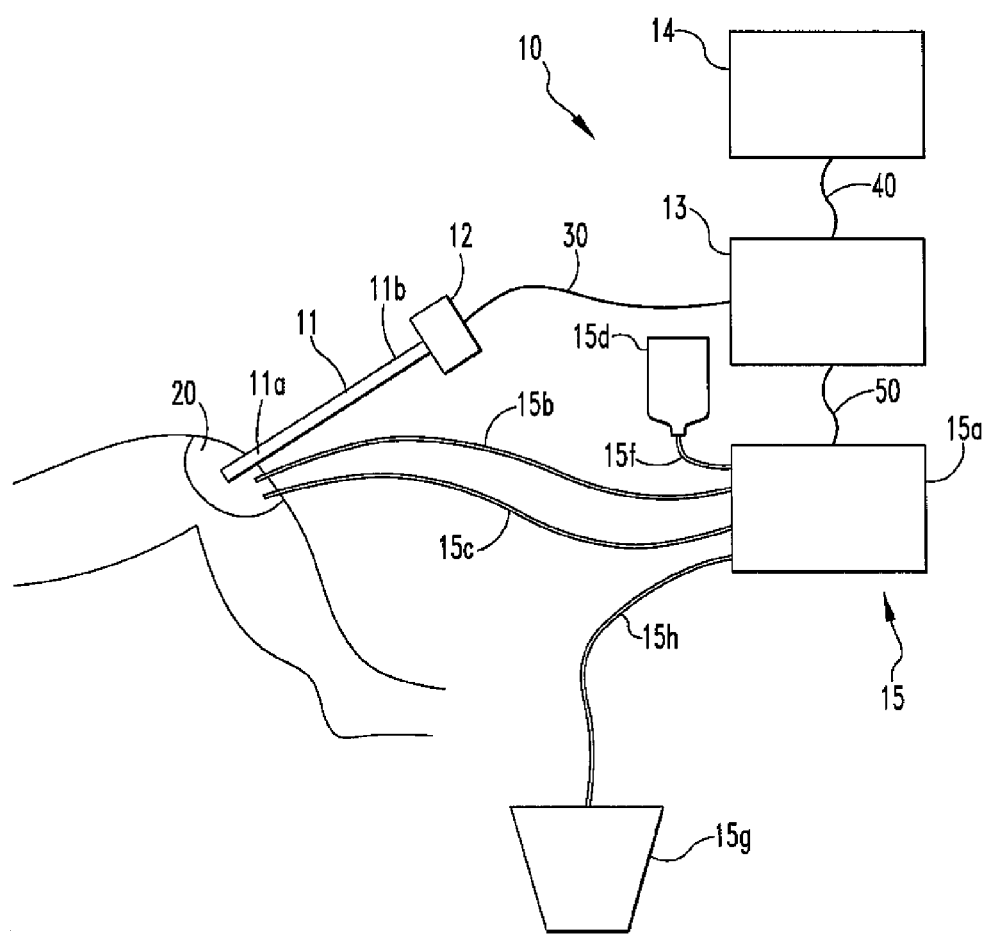

SYSTEM FOR USE IN SURGICAL PROCEDURES

CROSS REFERENCE TO RELATED APPLICATIONS

This application is a continuation of U.S. patent application Ser. No. 12/710,431 filed on Feb. 23, 2010 which claims priority to U.S. patent application Ser. No. 61/157,391 filed on Mar. 4, 2009, the disclosures of which are incorporated by reference in their entirety.

BACKGROUND

1. Technical Field

The present disclosure relates to systems for use in surgical procedures, such as endoscopic surgeries.

2. Related Art

Currently, during a surgical procedure, such as an endoscopic surgical procedure, an optical image from the surgical site is captured by an endoscope. The image is transmitted to an imaging device, such as a camera, that is coupled to the endoscope, processed, and then transmitted by the device to an imaging processor, such as a camera control unit. The imaging processor further processes the image before transmitting it to a display unit, such as a monitor. The image on the monitor is closely watched by the operating room staff so that when the image becomes unclear, manual adjustments can be made to restore a clear view of the image. For example, when bleeding occurs at the site and the image turns red, the surgeon, or another member of the surgical staff, makes manual adjustments to a fluid management unit, such as a fluid pump, in order to irrigate the site and restore the clear view of the image. This manual activity requires time and resources, thereby extending the amount of time the staff spends performing the surgery.

Therefore, a system is needed that allows for the imaging processor to detect when the image becomes unclear and responds by automatically communicating this information to, for example, a fluid management system, so that automatic adjustments can be made to the fluid management system in order to restore a clear image of the surgical site.

SUMMARY

In one aspect, the present disclosure relates to a system for use in surgical procedures. The system includes an endoscope; an imaging device coupled to the endoscope; an imaging processor coupled to the imaging device; and at least one management system coupled to the imaging processor, wherein a function of the management system is automatically adjusted upon receipt of a communication from the imaging processor.

In an embodiment, the endoscope is capable of transmitting an optical image to the imaging device. In another embodiment, the imaging device processes the optical image and transmits the image to the imaging processor. In yet another embodiment, the system further includes a display unit coupled to the imaging processor, wherein the imaging processor further processes the image and transmits the image to the display unit. In a further embodiment, adjustments to the management system allow for adjustments to the image transmitted to the display unit. In yet a further embodiment, the imaging device includes a camera. In an embodiment, the imaging processor includes a camera control unit. In another embodiment, the at least one management system includes a fluid management system.

In yet another aspect, the present disclosure relates to a method of adjusting an image of a surgical site during a surgical procedure. The method includes providing an endoscopic system comprising an endoscope; an imaging device coupled to the endoscope; an imaging processor coupled to the imaging device; at least one management system coupled to the imaging processor; and a display unit coupled to the imaging processor; and obtaining an image of the surgical site by viewing the surgical site with the endoscope, the image being transmitted by the imaging processor to the display unit, wherein a function of the management system is automatically adjusted upon receipt of a communication from the imaging processor, the adjustments to the management system allowing for adjustments to the image.

In an embodiment, the at least one management system includes a fluid management system.

Further areas of applicability of the present disclosure will become apparent from the detailed description provided hereinafter. It should be understood that the detailed description and specific examples, while indicating the preferred embodiment of the present disclosure, are intended for purposes of illustration only and are not intended to limit the scope of the disclosure.

BRIEF DESCRIPTION OF THE DRAWINGS

The accompanying drawings, which are incorporated in and form a part of the specification, illustrate the embodiments of the present disclosure and together with the written description serve to explain the principles, characteristics, and features of the disclosure. In the drawings:

FIG. 1 shows a first embodiment of the system of the present disclosure.

DETAILED DESCRIPTION OF THE EMBODIMENTS

The following description of the preferred embodiment(s) is merely exemplary in nature and is in no way intended to limit the invention, its application, or uses.

FIG. 1 shows a first embodiment of the system 10 of the present disclosure in use during endoscopic surgery. The system 10 includes an endoscope 11 with a first end 11a and a second end 11b. The first end 11a of the endoscope 11 is disposed within a body cavity 20, such as a joint cavity, and an imaging device 12, such as a camera, is coupled to the second end 11b of the endoscope 11. An imaging processor 13, such as a camera control unit, is coupled to the camera 12 via coupling means 30, such as a cable.

Coupled to the imaging processor 13 via separate coupling means 40,50 are a display unit 14, such as a monitor, and a management system 15, such as a fluid management system. The fluid management system 15 includes a fluid pump 15a and fluid inflow/fluid outflow lines 15b,15c coupled to the pump 15a. For the purposes of this disclosure, a single cartridge system that includes lines for both the inflow and the outflow is used. The cartridge is coupled to the pump 15a via coupling means. However, other systems may be used. A fluid source 15d, such as a saline bag or other fluid source, is coupled to the pump 15a, via a first tubing 15f and a waste container 15g is coupled to the pump 15a via a second tubing 15h.

During a surgical procedure, an optical image from the surgical site 20 is captured by optical lenses that are located within the endoscope 11. The image is transmitted to the camera 12, specifically to a sensor located within the camera 12, and is processed by the sensor resulting in an analog video signal. The analog video signal is converted to a digital video signal by an analog to digital converter, also located within the camera 12. The converter may be any analog to digital converter known to one of skill in the art. In addition to the converter, the camera 12 optionally may include a serializer-deserializer (SERDES). If the normal camera readout speed is maintained and the digital video signal is sent to the camera control unit 13 in parallel, an increase in the diameter of the coupling means 30 may be required, which may cause the coupling means 30 to be too large and inflexible. The use of a SERDES substantially reduces this possibility by serializing the signal and increasing the serial transmission rate.

Once the digital video signal is transmitted to the camera control unit 13, the signal is processed by a digital video signal processor located within the unit 13. The processed signal is then transmitted via the coupling means 40 to the monitor.

The digital video signal processor subdivides each field of data, contained within the signal, into regions of interest. Statistical information regarding these regions are provided by the processor to a microprocessor or video processor, which is also contained within the unit 13 and interfaces with the processor via a memory mapped interface. Other interfaces may also be used. The statistical information includes, but is not limited to Red, Green, Blue (RGB) value. The microprocessor converts the RGB value into Hue/Saturation/Value (HSV), via algorithms and other code that is stored within the microprocessor. Color space other than HSV, such as L*AB, may be converted from the RGB value. Subsequently, the microprocessor uses this HSV information to detect the presence and location of blood at the surgical area 20 by color (Hue) and determine the concentration of this blood by the intensity of color (Saturation). Once the concentration of the blood becomes high enough that the image on the monitor becomes unclear, this unclear image information will be automatically downloaded, via the coupling means 50, by the control unit microprocessor to a microprocessor located in the fluid management system 15.

Upon receipt of this information, a function of the fluid management system 15, such as fluid inflow or fluid outflow, is automatically adjusted to create a clear view of the image. For example, when bleeding occurs at the site 20 and the image turns red, the unit 13 downloads this information to the fluid management system 15 and pre-determined adjustments to the pump 15a pressure settings may be made. For example, fluid inflow to the site 20, via the fluid inflow line 15b, may occur in order to irrigate the site 20 and restore the clear view of the image. Alternatively, fluid outflow from the site 20, via the fluid outflow line 15c, may occur in order to withdraw fluid and restore the clear view of the image. These adjusted settings may last for a pre-determined length of time and automatically revert to the preceding settings or the adjusted settings may prevail until such time that the camera control unit 13 detects the level of red within the image to be below a pre-determined level, thereby sending a signal to the pump 15a to return its settings to the previous levels.

Furthermore, differential analysis of the statistics by the control unit microprocessor may help to distinguish between static red objects and moving objects, such as blood, at the surgical area 20. The microprocessor may evaluate the statistics per data field and/or process the differential change over multiple data fields to control the rate of fluid inflow and fluid outflow to and from the surgical area 20. Also, once the control unit 13 provides information to the fluid management system 15 that will actuate the system 15 (i.e., cause fluid inflow or fluid outflow to or from the area 20), the system 15 may send a communication to the unit 13 confirming receipt of this information and actuation of the system 15. In this respect, the communication between the control unit 13 and the fluid management system 15 constitutes a closed loop control system. Furthermore, once the unit 13 receives this confirmation, the unit 13 may subsequently send information about this actuation to the monitor 14, such that an on screen display is showcased on the monitor, thereby allowing the user to know that the system 15 was actuated.

Also, rather than transmitting information via cables 30, 40, 50, the transmission may be wireless via the use of radio frequency technology or other wireless technology. The communication software protocol used by the control unit 13 and the fluid management system 15 to communicate may be, but is not limited to, RS232 or TCP/IP.

In addition to the recognition of redness within the image, other colors or image attributes may be detected by the unit 13 for various other surgical reasons and automatically communicated to the fluid management system 15. Furthermore, other management systems and devices including, but not limited to, shaver control units, radiofrequency generators, and gas insufflators may be coupled to the unit 13 for detection and subsequent communication of attributes for recognition. For instance, a gas insufflator may be coupled to the unit 13 so that, during surgery, debris, such as tissue particles and air bubbles, may be detected by the unit 13 and communicated, via a signal, to the insufflator. Upon receipt of this information by the insufflator, pre-determined adjustments to the insufflator pressure settings may be made. For example, inflow of air or some other medical substance to the site 20 may occur in order to free the site 20 of debris and restore the clear view of the image.

As various modifications could be made to the exemplary embodiments, as described above with reference to the corresponding illustrations, without departing from the scope of the disclosure, it is intended that all matter contained in the foregoing description and shown in the accompanying drawings shall be interpreted as illustrative rather than limiting. Thus, the breadth and scope of the present disclosure should not be limited by any of the above-described exemplary embodiments, but should be defined only in accordance with the following claims appended hereto and their equivalents.

I claim:

1. A management system for use in surgical procedures in conjunction with an endoscope, an imaging device communicably coupled to the endoscope, and an imaging processor communicably coupled to the imaging device, the management system comprising:
   a fluid management system communicably coupleable to the imaging processor, the fluid management system having at least one specified function,
   wherein the specified function of the fluid management system is automatically adjusted upon receipt of a communication from the imaging processor in response to the detection of blood.

2. The management system of claim 1 wherein the fluid management system includes a fluid pump.

3. The management system of claim 2 wherein the fluid management system further includes fluid inflow and outflow lines coupleable to the fluid pump.

4. The management system of claim 3 wherein the fluid inflow and outflow lines are part of a cartridge system.

5. The management system of claim 4 wherein the fluid management system further includes coupling means operative to couple the cartridge system to the fluid pump.

6. The management system of claim 2 wherein the fluid pump is coupleable to a fluid source.

7. The management system of claim 6 wherein the fluid management system further includes a first tubing operative to couple the fluid pump to the fluid source.

8. The management system of claim 2 wherein the fluid pump is coupleable to a waste container.

9. The management system of claim 8 wherein the fluid management system further includes a second tubing operative to couple the fluid pump to the waste container.

10. A method for use in surgical procedures in conjunction with an endoscope, an imaging device communicably coupled to the endoscope, and an imaging processor communicably coupled to the imaging device, the method comprising:
   providing a fluid management system having at least one specified function;
   communicably coupling the fluid management system to the imaging processor; and
   automatically adjusting the specified function of the fluid management system upon receipt of a communication from the imaging processor in response to the detection of blood.

11. The method of claim 10 wherein the fluid management system includes a fluid pump, and wherein the method further comprises:
   coupling, by coupling means, fluid inflow and outflow lines to the fluid pump.

12. The method of claim 11 wherein the fluid inflow and outflow lines are part of a cartridge system.

13. The method of claim 11 further comprising:
   coupling the fluid pump to a fluid source.

14. The method of claim 11 further comprising:
   coupling the fluid pump to a waste container.

\* \* \* \* \*